United States Patent [19]

Shimizu et al.

[11] 4,334,066
[45] Jun. 8, 1982

[54] HETEROCYCLIC CONTAINING 5-OXO PYRANS

[75] Inventors: Yasuo Shimizu; Hisashi Takao, both of Tokushima; Shoji Asano, Kitamura; Shuya Shimada; Kazutoshi Kikkawa, both of Tokushima, all of Japan

[73] Assignee: Otsuka Kagaku Yakuhin Kabushiki Kaisha, Japan

[21] Appl. No.: 255,817

[22] Filed: Apr. 20, 1981

[51] Int. Cl.$^3$ .................................... C07D 295/10
[52] U.S. Cl. .................................. 544/149; 544/374; 546/207; 548/517
[58] Field of Search ............... 544/149, 374; 546/207; 260/326.5 D; 424/248.58, 250, 267, 274

[56] References Cited

U.S. PATENT DOCUMENTS 3,029,256  4/1962  Cook .................................... 544/149

OTHER PUBLICATIONS

Torii et al., *Chemical Abstracts*, vol. 88 (1978), No. 50593h.

Japanese Unexamined Patent Application No. 18578, Feb. 20, 1978.
Japanese Unexamined Patent Application No. 12166, Jan. 29, 1977.

*Primary Examiner*—Robert W. Ramsuer
*Attorney, Agent, or Firm*—Larson and Taylor

[57] ABSTRACT

A pyran derivative represented by the formula

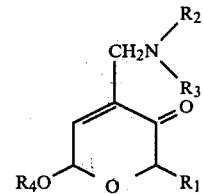

wherein $R_1$ and $R_4$ are each the same or different alkyl having 1 to 6 carbon atoms, $R_2$ and $R_3$, when attached to a nitrogen atom, forms a saturated hetrocyclic ring which has as a hetero atom a nitrogen atom is addition to the nitrogen atom attached to $R_2$ and $R_3$, or oxygen atom, and an acid addition salt thereof. The compounds have antibacterial and insecticidal action.

2 Claims, No Drawings

HETEROCYCLIC CONTAINING 5-OXO PYRANS

This invention relates to novel pyran derivatives and a process for preparing the derivatives.

The pyran derivatives of this invention are those represented by the formula

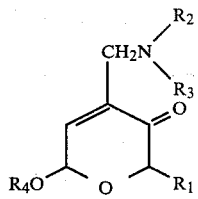

wherein $R_1$ and $R_4$ are each the same or different alkyl having 1 to 6 carbon atoms, $R_2$ and $R_3$, when attached to a nitrogen atom, forms a saturated heterocyclic ring which may have as a hetero atom a nitrogen atom in addition to the nitrogen atom attached thereto, or oxygen atom and acid addition salts thereof.

Examples of the alkyl groups having 1 to 6 carbon atoms and represented by $R_1$ and $R_4$ in the formula (I) are methyl, ethyl, propyl, isopropyl, butyl, t-butyl, pentyl, hexyl, etc. Exemplary of the group constituting the saturated hetrocyclic ring and represented by the group

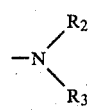

are morpholino, piperazino, piperidino, pyrrolidino, etc.

Japanese Unexamined Patent Publications Nos. 12166/1977 and 18578/1978 disclose the compounds similar to the pyran derivatives represented by the formula (I). These conventional compounds are useful as the intermediates for producing maltol derivatives. The compounds (I) of the present invention are different from such conventional compounds in the substituent on the pyran ring. We conducted research in an attempt to improve properties of pyran compounds and found in the course of the research that the compounds of the formula (I) have actions undisclosed in the aforesaid publications, such as an antibacterial action and insecticidal action including the action of killing fleas, bugs and like noxious insects, and thus are very useful as antibacterial agents, insecticides, vermin-controlling agents and particularly agricultural and horticultural chemicals producing such efficacies. These novel findings have matured to the present invention.

Table 1 shows typical examples of the pyran derivatives of this invention.

TABLE 1

| No. | $R_1$ | $-N\begin{matrix}R_2\\R_3\end{matrix}$ | $R_4$ |
|---|---|---|---|
| 1 | $C_2H_5$ | piperazino | $CH_3$ |
| 2 | iso-$C_3H_7$ | morpholino | $C_2H_5$ |
| 3 | $C_2H_5$ | azetidino | $C_2H_5$ |
| 4 | $CH_3$ | piperidino | $CH_3$ |
| 5 | $C_6H_{13}$ | piperazino | $C_2H_5$ |
| 6 | iso-$C_3H_7$ | morpholino | $C_6H_{13}$ |
| 7 | iso-$C_3H_7$ | azetidino | iso-$C_3H_7$ |

The compounds of the present invention can be prepared by various processes, for example, a process according to the following reaction equation.

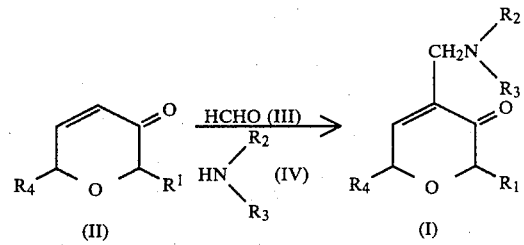

wherein $R_1$ to $R_4$ are as defined above.

In the above process, the conventional compound of the formula (II) are reacted with the formaldehyde of the formula (III) and the compound of the formula (IV) to prepare the compound (I) of the present invention.

The reaction for the preparation of the compound (I) is effected in methanol, ethanol, propanol or like lower alcohols. The compounds (III) and (IV) are used each in an amount of at least (mole, preferably 1 to 2 moles per mole of the compound (II). The reaction is carried out at 0° to 50° C., preferably at room temperature and completed in about 2 to about 6 hours.

The present compound thus prepared can be isolated from the reaction mixture for purification by a usual separation method, such as solvent extraction, solvent dilution, distillation, recrystallization, silica gel chromatography, etc.

Compounds of the present invention were tested for antibacterial properties. An example of the test, and examples for the preparation of the compounds of this invention will be given below.

Antibacterial test

Test Compounds

Compound 1 (shown in Table 1): 6-ethyl-2-methoxy-4-piperazinomethyl-5-oxo-5,6-dihydro-2H-pyran Compound 2 (shown in Table 1): 6-isopropyl-2-ethoxy-4-morpholinomethyl-5-oxo-5,6-dihydro-2H-pyran A 2% solution of Compound 1 in acetone is diluted with water to the desired concentration. A 1 ml quantity of the dilution is placed in a Petri dish, and mixed with 9 ml of the potato-dextrose-agar medium (hereinafter referred to as PDA medium) to prepare an agar plate. The same procedure is repeated by the use of Compound 2 except that the 2% solution of Compound 2 in acetone is diluted with water to a concentration different from that of the solution of Compound 1, whereby an agar plate different in concentration of the compound is prepared.

A test microorganism cultured in a PDA medium is stamped out on the front end by a cork borer 10 mm in diameter to obtain a disc of fungal mycelia, and the disc is placed, with the mycelia surface down, on each of the agar plates thus prepared.

By observing with the unaided eye 2 days later whether there is further growth of the mycelia, determined is the minimum inhibitory concentration (ppm) to inhibit completely the growth of the mycelia, and the minimum inhibitory concentrations as obtained for the test microorganisms are shown in Table 2. The test microorganisms employed are described below.

Test Microorganism

A ... Rice blast disease
(*Pyricularia oxyzae*)

B ... Anthracnose of cucumber
(*Colletotrichum lagenarium*)

C ... Stem rot of eggplant
(*Sclerotinia Sclerotiorum*)

D ... Gammy stem blight of melon
(*Mycosphaerella melonis*)

E ... Early blight of tomato
(*Alternaria solaui*)

F ... Bacterial blight of rice
(*Xanthomonas oryzae*)

TABLE 2

| Test Micro-organism | Minimum Inhibitory Concentration (ppm) | |
|---|---|---|
| | Test Comp. No. 1 | Test Comp. No. 2 |
| A | 100 | 100 |
| B | 50 | 100 |
| C | 100 | 100 |
| D | 100 | 100 |
| E | 200 | 200 |
| F | 12.5 | |

EXAMPLE 1

To 100 ml of methanol are added 19.8 g of 6-isopropyl-2-ethoxy-5-oxo-5,6-dihydro-2H-pyran, 7 g of 37% formalin and 9 g of morpholine. Then the mixture is stirred at room temperature for 4 hours. The reaction mixture is concentrated at reduced pressure and the residue is isolated and purified by silica gel column chromatography giving 23.6 g of light yellow oily 6-isopropyl-2-ethoxy-4-morpholinomethyl-5-oxo-5,6-dihydro-2H-pyran (compound No. 2 in Table 1). IR (neat) 1698 cm$^{-1}$ (C=O)

NMR (CDCl$_3$)

6.80 ppm (d, 1H, CH=C)

Elementary analysis (for C$_{15}$H$_{25}$O$_4$N)

| | C | H | N |
|---|---|---|---|
| Calcd. (%) | 63.71 | 8.96 | 5.12 |
| Found (%) | 63.58 | 8.89 | 4.94 |

EXAMPLE 2

The same procedure as in Example 1 is repeated, affording 6-ethyl-2-methoxy-4-piperazino methyl-5-oxo-5,6-dihydro-2H-pyran (Compound No. 1 in Table 1). The compound thus prepared is admixed with an HBr gas-saturated ethanol solution, and the mixture is allowed to stand at room temperature for 10 hours. The precipitated crystal is filtered off with suction and washed with a small amount of ethanol, giving 6-ethyl-2-methoxy-4-piperazino methyl-5-oxo-5,6-dihydro-2H-pyran hydrobromide, m.p. 135° to 138° C.

Elementary analysis (for C$_{13}$H$_{22}$O$_3$N$_2$ HBr)

| | C | H | N |
|---|---|---|---|
| Calcd. (%) | 46.71 | 6.98 | 8.31 |
| Found (%) | 46.58 | 6.92 | 8.36 |

EXAMPLES 3 to 7

Compounds Nos. 3 to 7 shown in Table 1 are prepared by the same procedure as in Example 1.

We claim:

1. A pyran derivative represented by the formula

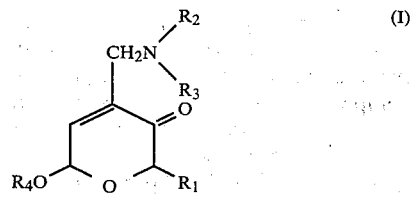

wherein R$_1$ and R$_4$ are each the same or different alkyl having 1 to 6 carbon atoms, R$_2$ and R$_3$, when attached to a nitrogen atom, forms a saturated heterocyclic ring which has as a hetero atom a nitrogen atom in addition to the nitrogen atom attached to R$_2$ and R$_3$, or oxygen atom, and an acid addition salt thereof.

2. A pyran derivative and an acid addition salt thereof as defined in claim 1 wherein the group

in the formula (I) is piperazino, morpholino, pyrrolidino or piperidino.

* * * * *